US010912861B2

(12) United States Patent
Higley et al.

(10) Patent No.: US 10,912,861 B2
(45) Date of Patent: Feb. 9, 2021

(54) SOFT-TACK, POROUS SUBSTRATES FOR HARVESTING SKIN GRAFTS

(71) Applicant: KCI Licensing, Inc., San Antonio, TX (US)

(72) Inventors: Kevin Higley, San Antonio, TX (US); Bradley Jonietz, San Antonio, TX (US); T. Blane Sanders, San Antonio, TX (US)

(73) Assignee: KCI LICENSING, INC., San Antonio, TX (US)

( * ) Notice: Subject to any disclaimer, the term of this patent is extended or adjusted under 35 U.S.C. 154(b) by 92 days.

(21) Appl. No.: 15/095,584

(22) Filed: Apr. 11, 2016

(65) Prior Publication Data

US 2016/0296663 A1 Oct. 13, 2016

Related U.S. Application Data

(60) Provisional application No. 62/145,342, filed on Apr. 9, 2015.

(51) Int. Cl.
*A61L 27/18* (2006.01)
*A61B 17/322* (2006.01)
(Continued)

(52) U.S. Cl.
CPC ............ *A61L 27/18* (2013.01); *A61B 17/322* (2013.01); *A61L 15/24* (2013.01); *A61L 15/26* (2013.01);
(Continued)

(58) Field of Classification Search
CPC .......... A61L 27/18; A61L 15/24; A61L 15/26; A61L 15/60; A61L 27/56; A61L 31/08;
(Continued)

(56) References Cited

U.S. PATENT DOCUMENTS 2,379,574 A 7/1945 Goldthwait
2,579,039 A 12/1951 Evans
(Continued)

FOREIGN PATENT DOCUMENTS

CN 2125374 U 12/1992
CN 2596950 Y 1/2004
(Continued)

OTHER PUBLICATIONS

[No Author Listed] BBC—GCSE Bitsize: Gore-Tex, Article: http://www.bbc.co.uk/schools/gcsebitesize/science/ocr_gateway_pre_2011/carbon_chem/6_designer_polyers3.shtml; retrieved Apr. 22, 2015.
(Continued)

*Primary Examiner* — George J Ulsh
(74) *Attorney, Agent, or Firm* — Foley & Lardner LLP

(57) ABSTRACT

Devices and methods for skin graft harvesting are disclosed. In one aspect of the invention, substrates for transplanting skin grafts are disclosed that include a soft-tack, biocompatible composition having a surface adapted to contact at least one excised skin graft and engage the graft for removal from a donor site. In another aspect of the invention, at least a portion of the skin-contacting surface of the substrate (or dressing) is porous to facilitate fluid transport into (or out of) the graft site during harvesting and/or transplantation. The substrates can also incorporate an absorbent component to capture fluids. The substrate can be a mesh or fabric or web, e.g. woven, knitted, nonwoven or molded. The substrate can be a mesh of biocompatible fibers, for example, cellulosic, polyolefins, polyurethanes, polyesters or polyamide fibers. In one embodiment the mesh is formed of cellulose acetate fibers and coated with a silicone gel, to imparted the desire degree of tackiness.

16 Claims, 6 Drawing Sheets

(51) Int. Cl.
*A61L 31/08* (2006.01)
*A61L 31/14* (2006.01)
*A61L 15/24* (2006.01)
*A61L 15/26* (2006.01)
*A61L 15/60* (2006.01)
*A61L 27/56* (2006.01)

(52) U.S. Cl.
CPC .............. *A61L 15/60* (2013.01); *A61L 27/56* (2013.01); *A61L 31/08* (2013.01); *A61L 31/146* (2013.01); *A61B 2017/3225* (2013.01)

(58) Field of Classification Search
CPC ................ A61L 31/146; A61B 17/322; A61B 2017/3225
See application file for complete search history.

(56) References Cited

U.S. PATENT DOCUMENTS

| | | |
|---|---|---|
| 2,721,555 A | 10/1955 | Jenny |
| 3,054,404 A | 9/1962 | Meek |
| 3,782,387 A | 1/1974 | Falabella |
| 4,345,374 A | 8/1982 | Jacobson |
| 4,600,533 A | 7/1986 | Chu |
| 4,605,010 A | 8/1986 | McEwen et al. |
| 4,666,447 A | 5/1987 | Smith |
| 4,679,324 A | 7/1987 | Krik |
| 4,773,418 A | 9/1988 | Hettich |
| 4,917,086 A | 4/1990 | Feltovich et al. |
| 5,015,584 A | 5/1991 | Brysk |
| 5,163,955 A | 11/1992 | Love et al. |
| 5,386,633 A | 2/1995 | Kanno |
| 5,433,221 A | 7/1995 | Adair |
| 5,441,490 A | 8/1995 | Svedman |
| 5,460,939 A | 10/1995 | Hansbrough |
| 5,476,478 A | 12/1995 | Jackson |
| 5,489,304 A | 2/1996 | Orgill |
| 5,496,339 A | 3/1996 | Koepnick |
| 5,545,222 A | 8/1996 | Bonutti |
| 5,571,098 A | 11/1996 | Domankevitz |
| 5,595,570 A | 1/1997 | Smith |
| 5,686,303 A | 11/1997 | Korman |
| 5,730,717 A | 3/1998 | Gelbfish |
| 5,759,193 A | 6/1998 | Burbank |
| 5,792,173 A | 8/1998 | Breen et al. |
| 5,817,115 A | 10/1998 | Nigam |
| 5,888,219 A | 3/1999 | Bonutti |
| 5,914,261 A | 6/1999 | Korman |
| 5,914,264 A | 6/1999 | Korman |
| 5,921,980 A | 7/1999 | Kiru |
| 5,972,476 A | 10/1999 | Field |
| 5,976,163 A | 11/1999 | Nigam |
| 6,056,738 A | 5/2000 | Marchitto |
| 6,063,094 A | 5/2000 | Rosenberg |
| 6,071,247 A | 6/2000 | Kennedy |
| 6,071,267 A | 6/2000 | Zamierowski et al. |
| 6,080,166 A | 6/2000 | McEwen et al. |
| 6,083,236 A | 7/2000 | Feingold |
| 6,248,114 B1 | 6/2001 | Ysebaert |
| 6,254,580 B1 | 7/2001 | Svedman |
| 6,358,260 B1 | 3/2002 | Ross |
| 6,364,908 B1 | 4/2002 | Ysebaert |
| 6,402,770 B1 | 6/2002 | Jessen |
| 6,436,078 B1 | 8/2002 | Svedman et al. |
| 6,585,939 B1 | 7/2003 | Dapprich |
| 6,612,310 B2 | 9/2003 | Sklar |
| 6,623,498 B1 | 9/2003 | Ziemer |
| 6,693,077 B1 | 2/2004 | Ruben et al. |
| 6,800,282 B1 | 10/2004 | Thomson |
| 6,860,904 B2 | 3/2005 | Bonutti |
| 7,056,327 B2 | 6/2006 | Levesque et al. |
| 7,078,582 B2 | 7/2006 | Stebbings |
| 7,137,979 B2 | 11/2006 | Conrad et al. |
| 7,207,998 B2 | 4/2007 | Feingold |
| 7,208,006 B2 | 4/2007 | Fleischman |
| 7,244,444 B2 | 7/2007 | Bates |
| 7,513,902 B2 | 4/2009 | Banbury et al. |
| 7,540,875 B2 | 6/2009 | Jessen |
| 7,625,384 B2 | 12/2009 | Eriksson |
| 7,651,507 B2 | 1/2010 | Mishra |
| 7,666,134 B2 | 2/2010 | Eriksson |
| 7,666,192 B2 | 2/2010 | Seegert |
| 7,708,746 B2 | 5/2010 | Eriksson |
| 7,727,760 B2 | 6/2010 | Guu et al. |
| 7,926,401 B2 | 4/2011 | Mishra |
| 8,002,779 B2 | 8/2011 | Barker et al. |
| 8,109,187 B2 | 2/2012 | Mishra |
| 8,162,957 B2 | 4/2012 | Mishra |
| 8,187,285 B2 | 5/2012 | Eriksson |
| 8,562,626 B2 | 10/2013 | Sabir |
| 8,617,181 B2 | 12/2013 | Sabir |
| 8,926,631 B2 | 1/2015 | Sabir |
| 9,173,674 B2 | 11/2015 | Sabir et al. |
| 2001/0029380 A1 | 10/2001 | Ysebaert |
| 2002/0052614 A1 | 5/2002 | GeBauer |
| 2002/0092529 A1 | 12/2002 | Rozier |
| 2003/0009185 A1 | 1/2003 | Jessen |
| 2003/0069571 A1 | 4/2003 | Treat et al. |
| 2003/0152909 A1 | 8/2003 | Miranti |
| 2003/0212357 A1 | 11/2003 | Pace |
| 2004/0097967 A1 | 5/2004 | Ignon |
| 2004/0172045 A1 | 9/2004 | Eriksson |
| 2004/0186498 A1 | 9/2004 | Barnes et al. |
| 2004/0215217 A1 | 10/2004 | Banbury |
| 2004/0225309 A1 | 11/2004 | Eriksson |
| 2004/0230215 A1 | 11/2004 | Eriksson |
| 2004/0237744 A1 | 12/2004 | Lin |
| 2005/0038520 A1 | 2/2005 | Binette |
| 2005/0076921 A1 | 4/2005 | Rozier |
| 2005/0101972 A1 | 5/2005 | Bhatavadekar |
| 2005/0221276 A1 | 10/2005 | Rozakis et al. |
| 2005/0234485 A1 | 10/2005 | Seegert |
| 2005/0244967 A1 | 11/2005 | Pearlman |
| 2006/0079852 A1 | 4/2006 | Bubb et al. |
| 2006/0141616 A1 | 6/2006 | Guu |
| 2006/0173087 A1 | 8/2006 | Hyde et al. |
| 2006/0258956 A1 | 11/2006 | Haberstich et al. |
| 2006/0271070 A1 | 11/2006 | Eriksson |
| 2006/0287696 A1 | 12/2006 | Wright et al. |
| 2007/0183974 A1 | 8/2007 | Pearlman |
| 2007/0255168 A1 | 11/2007 | Hiber et al. |
| 2008/0146980 A1 | 6/2008 | Rousso |
| 2009/0085286 A1 | 4/2009 | Grist et al. |
| 2009/0099122 A1 | 4/2009 | Klinman et al. |
| 2010/0012311 A1 | 1/2010 | Colongo |
| 2010/0042127 A1 | 2/2010 | Eriksson |
| 2010/0145360 A1 | 6/2010 | Eriksson |
| 2010/0152651 A1 | 6/2010 | Boyden et al. |
| 2010/0152750 A1 | 6/2010 | Memar |
| 2010/0286635 A1 | 11/2010 | Watson, Jr. |
| 2010/0310823 A1 | 12/2010 | Albertelli et al. |
| 2011/0009882 A1 | 1/2011 | Remsburg et al. |
| 2011/0077664 A1 | 3/2011 | Schulz |
| 2011/0230849 A1 | 9/2011 | Coulthard et al. |
| 2011/0251602 A1 | 10/2011 | Anderson |
| 2011/0264115 A1 | 10/2011 | Asrani |
| 2011/0282309 A1 | 11/2011 | Campbell et al. |
| 2012/0021186 A1 | 1/2012 | Schneider |
| 2012/0035618 A1 | 2/2012 | Sabir |
| 2012/0035619 A1 | 2/2012 | Sabir |
| 2012/0035620 A1 | 2/2012 | Sabir |
| 2012/0035699 A1 | 2/2012 | Sabir |
| 2012/0041430 A1 | 2/2012 | Anderson |
| 2012/0125798 A1 | 5/2012 | Baecker et al. |
| 2012/0136323 A1 | 5/2012 | Stasko et al. |
| 2012/0172894 A1 | 7/2012 | Sabir et al. |
| 2012/0197267 A1 | 8/2012 | Sabir |
| 2012/0201755 A1 | 8/2012 | Rozakis et al. |
| 2012/0201793 A1 | 8/2012 | Bellomo |
| 2012/0209226 A1 | 8/2012 | Simmons et al. |
| 2012/0244623 A1 | 9/2012 | Patel |
| 2012/0271320 A1 | 10/2012 | Hall |
| 2013/0041385 A1 | 2/2013 | Giovannoli |

(56) References Cited

U.S. PATENT DOCUMENTS

| | | |
|---|---|---|
| 2013/0145596 A1 | 6/2013 | Sabir et al. |
| 2013/0158627 A1 | 6/2013 | Gozani |
| 2013/0165837 A1* | 6/2013 | Addison ............. A61F 13/0283 602/44 |
| 2013/0204273 A1 | 8/2013 | Sabir et al. |
| 2014/0277454 A1 | 9/2014 | Locke et al. |
| 2015/0127077 A1 | 5/2015 | Hanan |
| 2015/0182241 A1 | 7/2015 | Pratt |
| 2015/0182242 A1 | 7/2015 | Pratt et al. |
| 2015/0196224 A1 | 7/2015 | Rusu et al. |
| 2016/0296663 A1 | 10/2016 | Higley et al. |
| 2017/0128096 A1 | 5/2017 | Asrani et al. |

FOREIGN PATENT DOCUMENTS

| | | |
|---|---|---|
| CN | 101053528 A | 10/2007 |
| EP | 0099748 A1 | 2/1984 |
| EP | 1092515 A1 | 4/2001 |
| EP | 1614404 A2 | 1/2006 |
| EP | 2837370 A1 | 2/2015 |
| JP | 2009-095476 A | 5/2009 |
| JP | 2012-196478 A | 10/2012 |
| SU | 772644 A1 | 10/1980 |
| WO | 1992011879 | 7/1992 |
| WO | 1995028886 | 11/1995 |
| WO | 1996018432 | 6/1996 |
| WO | 1996033768 | 10/1996 |
| WO | 1997020509 | 6/1997 |
| WO | 1998016158 | 4/1998 |
| WO | 2003020333 | 3/2003 |
| WO | 2003039382 | 5/2003 |
| WO | 2003049626 | 6/2003 |
| WO | 2003049783 | 6/2003 |
| WO | 03063680 A2 | 8/2003 |
| WO | 03068120 A1 | 8/2003 |
| WO | 03093418 A2 | 11/2003 |
| WO | 2004028584 A1 | 4/2004 |
| WO | 2004071313 | 8/2004 |
| WO | 2004075764 | 9/2004 |
| WO | 2004078032 | 9/2004 |
| WO | 2004105576 | 12/2004 |
| WO | 2005033273 | 4/2005 |
| WO | 2005046428 | 5/2005 |
| WO | 2007034438 A2 | 3/2007 |
| WO | 2007117488 | 10/2007 |
| WO | 2010014716 A1 | 2/2010 |
| WO | 2010036788 A2 | 4/2010 |
| WO | 2011038326 | 3/2011 |
| WO | 2011059441 | 5/2011 |
| WO | 2011075676 | 6/2011 |
| WO | 2012019094 | 2/2012 |
| WO | 2012019095 | 2/2012 |
| WO | 2012019096 | 2/2012 |
| WO | 2012019098 | 2/2012 |
| WO | 2012087376 A1 | 6/2012 |
| WO | 2012102812 | 8/2012 |
| WO | 2012145504 | 10/2012 |
| WO | 2013049052 A2 | 4/2013 |
| WO | 20140152319 A2 | 9/2014 |
| WO | 2016081386 A1 | 5/2016 |
| WO | 20160164890 A1 | 10/2016 |
| WO | 2017049215 A1 | 3/2017 |
| WO | 2017079439 A1 | 5/2017 |
| WO | 2017087163 A1 | 5/2017 |

OTHER PUBLICATIONS

Awad, Chinese Cupping: A Simple Method to Obtain Epithelial Grafts for the Management of Resistant Localized Vitiligo, American Society of Dermatologic Surgery, Inc., Dermatol Surg, (2008), 34(9):1186-1193.

Balaji et al., Isolation of a Novel Population of Multipotent Stem Cells From Epidermal Layer of Human Skin, Biology and Medicine, (2010), 2(2):57-67.

Examination Report dated Nov. 17, 2017; received in Australian Application No. 2014239891 3 pages.

Extended European Search Report dated Apr. 30, 2014 received in European Application No. 11815367.5, 7 pages.

European Examination Report dated Mar. 18, 2015 corresponding to European Application No. 11815368.3 (4 sheets.).

European Search Report dated Apr. 17, 2015 received in European Application No. 12855127.2, 3 pages.

Extended European Search Report dated Mar. 10, 2016 received in European Application No. 14769345.1, 7 pages.

Extended European Search Report dated Mar. 3, 2016 received in European Application No. 14771124.6, 7 pages.

International Search Report and Written Opinion dated Aug. 1, 2014 for International Application No. PCT/US2014/027237, 12 pages.

International Search Report and Written Opinion dated Dec. 16, 2011 for International Application No. PCT/US11/46737, 8 pages.

International Search Report and Written Opinion dated Dec. 16, 2011 for International Application No. PCT/US11/46738, 6 pages.

International Search Report and Written Opinion dated Dec. 23, 2011 for International Application No. PCT/US11/46739, 6 pages.

International Search Report and Written Opinion dated Dec. 6, 2011 for International Application No. PCT/US11/46741, 6 pages.

International Search Report and Written Opinion dated Feb. 15, 2013 for International Application No. PCT/US2012/068551, 9 pages.

International Search Report and Written Opinion dated Jun. 28, 2016 for PCT/US2016/026918, 10 pages.

International Search Report and Written Opinion dated Mar. 19, 2015 for PCT/US2014/072170, 12 pages.

International Search Report and Written Opinion dated Mar. 19, 2015 for PCT/US2014/072188, 12 pages.

International Search Report and Written Opinion dated Mar. 20, 2015 for PCT/US2014/072180, 10 pages.

International Search Report and Written Opinion dated Oct. 2, 2014 for International Application No. PCT/US2014/027205, 19 pages.

International Search Report and Written Opinion dated Feb. 10, 2017 for International Application No. PCT/US2016/060336, 14 pages.

Invitation to Pay Additional Fees and, Where Applicable, Protest Fees dated May 26, 2017 for International Application No. PCT/US2017/018431, 20 pages.

Kreis et al., Expansion techniques for skin grafts: comparison between mesh and Meek Island (sandwich-) grafts, Burns, (1994), 20(1):S39-S42.

Lari et al., Expansion technique for skins grafts (Meek technique) in the treatment of severely burned patients, Burns, (2001), 27:61-66.

Meek et al., Successful Microdermagrafting Using the Meek-Wall Microdermatome, Am J Surg, (1958), 96(4):557-558.

Mulekar et al., Treatment of Vitiligo on Difficult-to-Treat Sites Using Autologous Noncultured Cellular Grafting, Dermatol Surg., (2009), 25(1):66-71.

Office Action dated Dec. 18, 2014 for U.S. Appl. No. 13/120,799.

Office Action dated Feb. 17, 2015 with English Text of Office Action corresponding to Japanese Patent Application No. 2013-523359, 2 pages.

Sams et al.. Useful adjuncts to harvest split-thickness skin grafts. Dermatol Surg. Dec. 2004;30(12 Pt 2):1591-2.

Weyandt et al., Split-skin grafting from the scalp: the hidden advantage. Dermatol Surg. Dec. 2009;35(12):1873-9.

International Search Report dated Jul. 26, 2017 for corresponding PCT/US2017/018431, pp. 8.

International Written Opinion dated Jul. 26, 2017 from corresponding PCT/US2017/018431, pp. 17.

Extended European Search Report received in EP Application No. 17186324.4 dated Nov. 20, 2017; 7 pages.

Office Action dated Jan. 3, 2018 issued in related Chinese Patent Application No. 2016104166749, 6 pages.

Negative Pressure Instrument Operating and Maintenance Information for Models NP-2, NP-4 and NP-V Apr. 30, 2004.

(56) References Cited

OTHER PUBLICATIONS

Office Action dated Oct. 12, 2018 issued in related Chinese Patent Application No. 2016104166749, 13 pages.
Office Action dated Feb. 24, 2018 issued in related Chinese Patent Application No. 2014800755616, 16 pages.
Examination Report dated Oct. 10, 2018 from corresponding EP Application No. 16 718 801.0, 4 pages.
Search Report dated Nov. 27, 2018 from corresponding EP Application No. 18 17 4326.1, 8 pages.
Office Action dated Jul. 3, 2018 issued in related Japanese Patent Application No. 2016-502336, 5 pages.
European Summons dated Oct. 31, 2019 for 16718801.0, 4 pages.
Meuleneire, "Soft silicone dressings made easy", Wounds International, May 1, 2013 (May 1, 2013), 6 pages.
International Search Report and Written Opinion dated Oct. 29, 2019 for PCT/US2019/045216, 14 pages.
Canadian Examination Report, CA2982203, dated Dec. 31, 2019, 3 pages.
European Extended Search Report, 19201750.7, dated Feb. 4, 2020, 7 pages.
International Search Report and Written Opinion dated Sep. 14, 2018 for International Application No. PCT/US2018/041399, 11 pages.
International Search Report and Written Opinion dated Apr. 25, 2019 for International Application No. PCT/US2019/015504, 12 pages.
International Search Report and Written Opinion dated Apr. 2, 2019 for International Application No. PCT/US2019/015230, 10 pages.
Ashley L. Howarth et al: "A novel approach to graft loss in burn using the CelluTome(TM) epidermal harvesting system for spot grafting: A case report", BURNS., vol. 41, No. 6, Sep. 1, 2015 (Sep. 1, 2015), pp. e57-e60.
Hachach-Haram: "The use of epidermal grafting for the management of acute wounds in the outpatient setting", Journal of Plastic, Reconstructive & Aesthetic Surgery, Jan. 1, 2015 (Jan. 1, 2015), pp. 1317-1318.
Ozay Ozkaya, et al: "The effect of nonpreserved human amniotic membrane on the survival of ischaemic skin flaps in rats", Journal of Plastic, Reconstructive and Aesthetic Surgery, vol. 65, No. 12, Dec. 1, 2012 (Dec. 1, 2012), pp. 1700-1705.
International Search Report and Written Opinion dated Mar. 29, 2019 for International Application No. PCT/US2018/065815, 13 pages.
International Search Report and Written Opinion dated Feb. 20, 2019 for International Application No. PCT/US2018/062973, 14 pages.

* cited by examiner

SOFT-TACK, POROUS SUBSTRATES FOR HARVESTING SKIN GRAFTS

CROSS-REFERENCE AND RELATED APPLICATIONS

This application claims benefit of U.S. Provisional Patent Application Ser. No. 62/145,342 filed Apr. 9, 2015, which is incorporated herein by reference in its entirety.

FIELD

The present invention relates generally to medical treatments and, more particularly, but not by way of limitation, to apparatus, systems, and methods for harvesting and transplanting skin grafts.

BACKGROUND

Skin is the largest organ of the human body, representing approximately 16% of a person's total body weight. Because it interfaces with the environment, skin has an important function in body defense, acting as an anatomical barrier from pathogens and other environmental substances. Skin also provides a semi-permeable barrier that prevents excessive fluid loss while ensuring that essential nutrients are not washed out of the body. Other functions of skin include insulation, temperature regulation, and sensation. Skin tissue may be subject to many forms of damage, including burns, trauma, disease, and depigmentation.

Skin grafts are often used to repair such skin damage. Skin grafting is a surgical procedure in which a section of skin is removed from one area of a person's body (autograft), removed from another human source (allograft), or removed from another animal (xenograft), and transplanted to a recipient site of a patient, such as a wound site. As with any surgical procedure, skin grafting involves certain risks. Complications may include graft failure, rejection of the skin graft, bleeding, fluid accumulation or infection at either the donor or recipient site. Additionally, when an autograft is taken from one area of a person's body to produce the graft, some degree of trauma occurs at the donor site. If the recipient site is a large wound or otherwise damaged skin region, the trauma at the donor site can be significant.

Techniques have been developed for harvesting a large number of smaller grafts, e.g., so-called micrografts, to reduce the trauma at the donor site. By removing only a fraction of the skin at a donor site and leaving regions of healthy skin surrounding the excised regions, a large amount of skin for transplantation can be obtained with less discomfort. Micrograft harvesting can also reduce the healing time and risk of infection.

Harvesting of skin grafts can be accomplished in many different ways. One common technique for harvesting a skin graft involves the application of suction to separate a surface portion of the skin, e.g., the epidermis and a basal cell layer, from the underlying dermis. Harvesting of suction blisters typically also involves a heat source to facilitate blister formation.

Various devices are available for generating and harvesting micrografts. For example, the CelluTome® skin harvester is available from Acelity, Inc. of San Antonio, Tex. The CelluTome® system includes a head that provides a source of reduced pressure (vacuum), and optionally a heater element, and a harvester configured for placement on a target region of a patient's skin. The harvester is further adapted to form a sealing engagement with the head such that the target region of skin is embraced within an evacuated chamber. The CelluTome® harvester further includes at least one alignment plate having a plurality of holes through which skin blisters can be raised in the presence of negative pressure; and a cutting plate having at least one cutting surface for cleaving skin blisters after they are formed within the chamber.

Typically, micrograft harvesters rely upon a support or substrate to lift the excised blisters from the device. The substrate is then applied to a recipient site so that the plurality of micrografts can be assimilated as transplanted tissue. Ideally, the grafts will expand and coalesce to complete the healing process.

SUMMARY

Devices and methods for skin graft harvesting are disclosed. In one aspect of the invention, substrates for transplanting skin grafts are disclosed that include a soft-tack, biocompatible composition having a surface adapted to contact at least one excised skin graft and engage the graft for removal from a donor site. In another aspect of the invention, at least a portion of the skin-contacting surface of the substrate (or dressing) is porous to facilitate fluid transport into (or out of) the graft site during harvesting and/or transplantation.

In one embodiment of the invention, the transport substrate can be used in conjunction with a skin micrograft harvester, such as the CelluTome® harvester to capture and retain a plurality of skin micrografts (or "microdomes"). The invention can utilize a flexible mesh that is coated, for example, with silicone, e.g. a silicone gel. The soft silicone, although not an adhesive, has a soft tack which when pressed onto microdomes, allowing for the slight immersion of the top of the microdome into the silicone, enabling the microdomes to be lifted away from the harvester. Due to the soft tack, the dressing can be lifted and repositioned as required. If the dressing folds over onto itself, it can be easily unfolded for the application. The open areas of the dressing mesh is sufficient for passage of fluid through the open areas to a secondary absorbent dressing, but is tight enough to prevent the microdomes from falling through the open areas.

Soft tack, mesh or porous substrates has several advantages over solid adhesive films in harvesting micrographs. For example, the soft tack nature of the substrates of the present invention permit unfolding and repositioning. Moreover, solid substrates (typically non-porous acrylic films) are often ill-suited for wet environments and do not permit fluid passage.

The substrate can be a mesh or fabric or web, e.g. woven, knitted, nonwoven or molded. In certain embodiments the substrate can be a mesh of biocompatible fibers. The fibers, for example, can be cellulosic, polyolefins, polyurethanes, polyesters or polyamides. In one embodiment the mesh is formed of cellulose acetate fibers.

The meshes are typically coated, e.g., with a silicone gel, to impart the desire degree of tackiness. For example, silicone coating compositions can be formed using silicone elastomers available from Dow Corning under product reference Q7-9177. Additional details on applying silicone coatings can be found in U.S. Patent Application Pub. No. 2013/0165837 by Systagenix Wound Management IP Co. BV entitled "Silicone Gel-Coated Wound Dressings," published Jun. 27, 2013, herein incorporated in its entirety by reference.

Following coating, the substrates should remain porous, e.g., apertures should remain between the coated fibers or web. The "open area" of the coated substrate can range from 5% to 65%, more preferably in some instances from 10% to 50%. The average diameter of individual apertures or pores can range from 0.3 to 4 mm, more preferably in some instances from 0.5 to 2 mm. The apertures should be smaller enough that skin micrografts that contact the substrate cannot easily pass through the apertures.

In certain embodiments the substrate is a fabric such as a gauze, or a mesh, having an array of apertures. The size and shape of the apertures in the substrate are not critical, but the apertures should suitably be such as to ensure that the material can be adequately coated with silicone gel without them becoming occluded. The apertures generally have an aspect ratio of from 1:1 to 5:1, and preferably from 1:1 to 2:1. For example, the apertures may be approximately circular or approximately square. The apertures suitably have an average diameter of from 0.3 to 4 mm, and more suitably from 0.5 to 2 mm.

The substrate can be formed from any medically acceptable material, such as cellulose, polyolefins, polyesters, or polyamides. An especially suitable material is cellulose acetate gauze. Substrates having a weight of from 15 to 200 $g/m^2$ are generally found to be suitable for use in the products of the invention, and fabrics weighing from 50 to 150 $g/m^2$ are most suitable. For example, certain embodiments employ a fabric of from 80 to 120 $g/m^2$.

Suitably, the silicone-coated substrate product retains open apertures to allow passage of wound fluid through the coated substrate. For example, an array of apertures may extend through said silicone coatings and the substrate layer. The open area of the coated substrate in the final product can, for example, be from about 1% to about 70%, or from about 10% to about 50%.

The substrate materials of the invention are characterized by a tacky silicone coating on at least one surface the substrate, the surface that is intended to capture one or more harvested skin grafts. This surface is typically referred to herein as the lower surface. However, it will be appreciated by those skilled in the art that orientation is simply for convenience sake and that the actual orientation of the soft tack surface will depend upon the orientation of the skin graft harvester.

In certain applications it can be simpler to form a substrate having a soft-tack composition on both the lower and the opposing upper surfaces. The tackiness of the two surfaces can be same or different. For example, the upper surface can be formed so as to be less or more tacky. In other embodiments the upper surface can be further treated or further coated to render it substantially non-sticky or, as described further below, the upper surface can be joined to an absorbent material to remove fluids during a subsequent transplantation stage.

The total coating weight of the tacky silicone (combined upper and lower layers) is suitably from about 50 $g/m^2$ to about 500 $g/m^2$, for example from about 80 $g/m^2$ to about 200 $g/m^2$, typically from about 100 $g/m^2$ to about 150 $g/m^2$. The silicone is suitably a soft skin adhesive silicone composition. Suitably chemistry is described below. The silicone is suitably hydrophobic.

One or both surfaces can be protected before use by cover sheets adhered to the coating by the tackiness thereof. In certain embodiments, one cover sheet can be removed more easily than the other. For example, one can selectively remove the first cover sheet if it is less strongly adhered in order to attach the substrate to a harvester apparatus to capture micrografts. Following graft capture, then the second cover sheet with its more-adherent surface can be removed to expose the other surface for application of secondary dressing layers, such as absorbent layers prior to transplantation of the graft at a recipient site. In other embodiments, both the upper and lower protective covers can be removed before harvesting the grafts because the soft-tack compositions can be designed such that they do not wrinkle or bend when applied to the harvester apparatus, and can be easily unfolded if needed.

The products of the invention may be made into wound dressings for application to the surface of a wound by removing the top and bottom cover sheets. Suitably, the products of the invention consist essentially of the substrate, the silicone coatings, and the cover sheets. Suitably, the products of the invention are sterile and packaged in a microorganism-impermeable container.

In certain embodiments the substrate includes a patterned base or a peripheral rim configured for positioning the substrate in a chamber of a skin graft harvesting device and, optionally, the substrate is further configured to capture a plurality of skin grafts at the same time.

In certain embodiments, the substrate has an average thickness between about 50 microns and about 10 millimeters, preferably in some cases, between about 500 microns ($\mu m$) and about 1000 microns ($\mu m$). The substrate should also be flexible enough to conform to the shape of the harvester and/or the recipient site. For example, the substrate can have a stiffness between about 5 Shore OO and about 80 Shore OO.

In another aspect of the invention, methods of making a material for capturing harvested skin graft are disclosed including, for example, the steps of providing a substrate layer having an upper surface and a lower surface; coating said upper and lower surfaces of said substrate layer with a fluid silicone prepolymer composition; followed by thermally partially curing said silicone prepolymer composition to produce an intermediate material having a partially cured silicone composition on said upper and lower surfaces; followed by further curing said partially cured silicone composition by exposing said intermediate material to ionizing radiation, to produce a final material having tacky silicone coatings on said upper and lower surfaces In certain embodiments it can be desirable to apply unequal weights of the silicone coating composition to the upper and lower surfaces, and/or to apply different amounts of heat to the upper and lower surfaces during curing, such that the silicone coatings on the upper and lower surfaces having different tackiness are formed.

In another aspect of the invention, methods of harvesting skin grafts are disclosed including the steps of placing a skin graft harvester at a donor site of a patient's skin, coupling the harvester to a source of reduced pressure such that the donor site of skin is embraced within an evacuated chamber and one or more blisters are raised through apertures in a cutter mechanism, placing a soft-tack, porous substrate having a surface adapted to couple with the cutter mechanism in contact the raised blister(s), actuating the cutter assembly to excise one or more blisters for use as skin grafts, and removing the substrate with the skin grafts attached thereto.

In yet another aspect of the invention, systems are disclosed that can include a soft-tack porous substrate and a disposable harvester head assembly that are provided separately or as a kit to facilitate skin harvesting. For example, the system can include a harvester head assembly configured for placement at a donor site of a patient's skin and further adapted for coupling to a source of reduced pressure such that the donor site of skin is embraced within an evacuated chamber, the harvester further comprising a cutter mechanism for excising skin grafts that are raised by reducing the pressure within the chamber; and a soft-tack, porous substrate having a surface adapted to couple with the cutter mechanism to contact at least one excised skin graft and engage said graft for removal from the harvester.

In a further aspect of the invention, the soft-tack, porous substrates of the present invention can be used in conjunction with a secondary absorbent component when the micrografts are ready for transplantation. The secondary component can be a separate element or it can be integral with the substrate, e.g. present during harvesting. In according with this aspect of the invention, dressings for transplanting skin grafts are disclosed including a base layer comprising a soft-tack, porous material adapted to contact at least one excised skin graft and to engage said graft for removal from a donor site; a cap member peripherally joined to the base layer and defining an enclosure therebetween; and an absorbent material disposed within the enclosure; wherein at least a portion of the base layer is porous and in fluid communication with the absorbent layer to capture fluids. The base layer can be a substrate composition, e.g., a silicone coated gauze material, as described above.

More generally, the base layer of the absorbent dressing preferably includes a soft-tack, biocompatible material, e.g., a material selected from the group of silicones, silicone gels, soft silicones, hydrocolloids, hydrogels, polyurethanes, polyurethane gels, polyolefins, polyolefin gels, hydrogenated styrenic copolymers, hydrogenated styrenic copolymer gels, foamed gels and combinations thereof that provides the desired degree of tackiness.

The skin graft contacting portion of the base layer in absorbent dressing embodiments can have dimensions similar to the stand-alone substrate. For example, the baser layer can have an average thickness between about 50 microns and about 10 millimeters, preferably in some cases, between about 500 microns (μm) and about 1000 microns (μm). The skin graft contacting portion of the base layer should also be flexible enough to conform to the shape of the harvester and/or the recipient site. For example, the skin graft contacting portion of the base layer can have a stiffness between about 5 Shore OO and about 80 Shore OO.

The base layer in absorbent dressing embodiments can include a plurality of openings to provide passageways for fluid transport from the recipient site to the absorbent material. The openings (e.g., pores) can be spaced apart from each other. In certain embodiments, the openings are generally circular. The openings can have an average cross-sectional dimension ranging from about 0.1 nanometers to about 1 millimeter, or preferably an average cross-sectional dimension ranging from about 1 nanometer to about 100 micrometers. In other embodiments, the pores can be elongated or grid-like and their minor dimension can range from about 0.1 nanometers to about 1 millimeter, or preferably from about 1 nanometer to about 100 micrometers.

The base layer in absorbent dressing embodiments can be patterned to define a plurality of skin graft capture sites and the base layer further includes a network of pores disposed between at least some of the capture sites. Again, the pores (disposed between capture sites) can be circular or elongated and have an average cross-section dimension (or a minor dimension, in the case of elongated pores) ranging from about 0.1 nanometers to about 1 millimeter, or preferably ranging from about 1 nanometers to about 100 micrometers.

The absorbent dressing component can also include at least one wicking layer disposed in the enclosure and adapted to distribute fluid to the absorbent material. For example, the substrate can include at least a first wicking layer disposed in the enclosure between the base layer and the absorbent material. Alternatively, or in addition to the first wicking layer, the substrate can include one or more additional wicking layers (e.g., a second wicking layer) disposed in the enclosure between the absorbent material and the sealing member. In certain embodiments, the first and/or second wicking layer can have a grain structure adapted to wick fluid along a surface of the wicking layer.

The absorbent material can further include a plurality of absorbent layers, and one or more of the additional absorbent layers can be positioned in fluid communication between a first wicking layer and a second wicking layer. The dressing can also include at least one intermediate wicking layer disposed in fluid communication between the absorbent layers. In certain embodiments, a peripheral portion of a first wicking layer can be coupled to a peripheral portion of a second wicking layer to provide a wicking layer enclosure surrounding the absorbent layer between the first and the second wicking layers.

In another embodiment of the invention, the absorbent material can include a hydrophilic material that is adapted to absorb fluid and the cap (or sealing) member can be liquid impermeable. For example, the sealing member can include a water-impermeable polyurethane component. In yet another embodiment of the invention, the dressing can further include at least one port for coupling to the reduced pressure source to extract accumulated fluids from the recipient site. The port can further include a valve, e.g., a check valve or one-way valve, to prevent backflow of extracted fluids. The port can further include a conduit providing fluid communication between the absorbent material or at least one wicking layer within the chamber and an external fluid receptacle.

The dressing can include at least one removable backing for handling the substrate prior to positioning it in a skin graft harvester. The substrate can further include another removable backing for handling the dressing prior to positioning it at a recipient site. For example, the substrate can include at least a first removable backing associated with the base layer for handling the substrate prior to positioning it in a skin graft harvester and a second removable backing for handling the dressing and an associated skin graft prior to positioning it at a recipient site.

In another aspect, a system is provided for draining a skin transplantation site including a substrate or dressing and a reduced-pressure source. The substrate or dressing is adapted to provide reduced pressure and/or to store fluid extracted from the site. The substrate or dressing includes a soft-tack base layer, an adhesive, a sealing member, a first wicking layer, a second wicking layer, an absorbent layer, and a conduit interface. The base layer has a periphery surrounding a central portion and a plurality of apertures disposed through the periphery and the central portion. The central portion of the base layer is adapted to be positioned proximate the transplantation site and the periphery of the base layer is adapted to be positioned proximate the tissue surrounding the transplantation site. Further, the periphery of the base layer is adapted to surround the transplantation site, and the apertures in the base layer are adapted to be in fluid communication with site and the tissue surrounding the transplantation site. (A two-part lower backing can also be employed such that a first (inner) portion of the lower backing is removed when the substrate is joined to a skin graft harvester and a second outer portion of the backing subsequently removed to facilitate peripheral adhesion at the transplantation site.) The sealing member has a periphery and a central portion, the periphery of the sealing member being positioned proximate the periphery of the base layer such that the central portion of the sealing member and the central portion of the base layer define an enclosure. The first wicking layer and the second wicking layer are each disposed in the enclosure. The absorbent layer is positioned in fluid communication between the first wicking layer and the second wicking layer. The conduit interface is positioned proximate to the sealing member and in fluid communication with the dressing. The reduced-pressure source is adapted to be coupled in fluid communication with the conduit interface to provide reduced pressure to the dressing.

In another aspect of the invention, methods are disclosed for fluid management during skin transplantation. The methods can include the steps of contacting at least one skin graft with an absorbent substrate, the substrate comprising a soft-tack base layer having a surface adapted to contact and engage at least one excised skin graft and a sealing member peripherally joined to the base layer and defining an enclosure therebetween; and an absorbent material disposed within the enclosure; deploying the substrate at a recipient site such that a skin graft that is engaged by the base layer contacts the recipient site; and maintaining the substrate in contact with the recipient site to facilitate transplantation of the graft and removal of fluids.

In another aspect, the methods of the present invention can include maintaining the absorbent substrate at the recipient site, and further, removing excess fluids at the recipient site by extraction into the absorbent material of the substrate. The methods can be practiced by providing a plurality of pores in the soft-tack base layer to provide a fluid communication path between a recipient site and the absorbent material within the substrate and, optionally, deploying at least one wicking layer within the substrate to distribute fluids captured from a recipient site to different regions of the absorbent material.

In certain embodiments, the methods can further include a step of coupling the substrate to a reduced pressure source to facilitate fluid extraction and, optionally, draining accumulated fluids from the absorbent material into a fluid extraction receptacle or deploying a one-way valve between the absorbent material and the fluid extraction receptacle.

Other aspects, features, and advantages of the illustrative embodiments will become apparent with reference to the drawings and detailed description that follow.

BRIEF DESCRIPTION OF THE DRAWINGS

A more complete understanding of this specification may be obtained by reference to the following detailed description when taken in conjunction with the accompanying drawings wherein.

DETAILED DESCRIPTION

Figure 1:
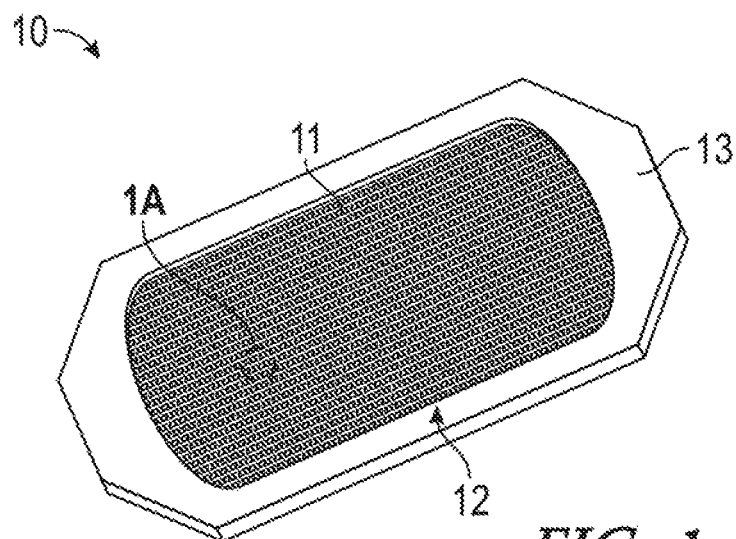
FIG. 1 is a schematic, perspective view of an illustrative embodiment of a soft-tack porous substrate for skin graft harvesting.

In the following detailed description of non-limiting, illustrative embodiments, reference is made to the accompanying drawings that form a part hereof. Other embodiments may be utilized and logical, structural, mechanical, electrical, and chemical changes may be made without departing from the scope of this specification. To avoid detail not necessary to enable those skilled in the art to practice the embodiments described herein, the description may omit certain information known to those skilled in the art. The following detailed description is not to be taken in a limiting sense, with the scope of the illustrative embodiments being defined by the appended claims.

The terms "micrograft" and "microdome" are used interchangeably herein and are intended to encompass skin grafts that have a width or length less than a millimeter, more preferably, less than 100 microns. A micrograft or microdome is an excised skin segment having at least one dimension parallel to the skin surface that is less than a millimeter, preferably less than 100 micrometers, more preferably in some applications less than 10 micrometers. The minimum width or length is preferably less than 500 micrometers, preferably less than 100 micrometers or less than 50 micrometers or less than 10 micrometers or less than 1 micrometer. For example, a micrograft or microdome can be generally circular, oval or oblong in a plane parallel to the skin surface and have a diameter or major axis that ranges from about 1 millimeter to 0.01 micrometers, or from about 100 micrometers to about 0.1 micrometers, or more preferably from about 50 to 1 micrometers. Micrografts and microdomes also typically have a depth dimension that extends at least through the epidermis and preferably in some applications encompasses at least one layer of basal cells. The depth can range from about 500 micrometers to about 0.1 micrometers, preferably from about 100 micrometers to about 1 micrometer.

The term "harvesting" as used herein is intended to encompass the removal of one or more skin grafts from an skin graft generating device, such as, for example, a suction blister micrograft generator, as well as the transplantation of such skin grafts and any intermediate steps, such as culturing, expanding, stretching, treating or otherwise preparing a skin graft for transfer to a recipient site.

The terms "substrate" and "dressing" are used interchangeably throughout the specification. The term "dressing" is typically used when the substrate is used not only to capture excised skin grafts but also to retain them for transplantation. During the transplantation the substrate (or dressing) with its captured grafts can be applied directly to a recipient site. Both substrates and dressings can also encompass other elements in addition to a soft-tack, porous surface, e.g., fluid absorbent layers or cap layers.

The terms "porous" as used herein is intended to encompass not only apertures or holes but also permeable and open cell structures, generally. The terms "generally circular" and "circular" are used interchangeably herein to describe openings that are round, oval or otherwise form closed polygonal shapes having a major dimension (width or diameter) that is less than 5 times the minor dimension (width or diameter) of the shape. Preferably the major dimension is less than 3 times, or less than 2 times, the minor dimension. In certain embodiments, a permeable or porous composition can be formed from woven or non-woven (e.g., matted) fibers. The fibrous base layer can include microfibers and/or nanofibers. In certain embodiments, microfibers having an average diameter of about 0.1 to about 10 micrometers can be desired. In other embodiments, nanofibers having an average diameter of about 1 to about 100 nanometers, preferably about 20 to about 80 nanometers, although in some instances, fibers with diameters about 1 to about 20 nanometers, can also be advantageous.

The term "about," as used herein, refers to variations in a numerical quantity that can occur, for example, through measuring or handling procedures in the real world; through inadvertent error in these procedures; through differences in the manufacture, source, or purity of compositions or reagents; and the like. Typically, the term "about" as used herein means greater or lesser than the value or range of values stated by $\frac{1}{10}$ of the stated values, e.g., ±10%. For instance, a concentration value of about 30% can mean a concentration between 27% and 33%. The term "about" also refers to variations that would be recognized by one skilled in the art as being equivalent so long as such variations do not encompass known values practiced by the prior art. Each value or range of values preceded by the term "about" is also intended to encompass the embodiment of the stated absolute value or range of values. Whether or not modified by the term "about," quantitative values recited in the claims include equivalents to the recited values, e.g., variations in the numerical quantity of such values that can occur, but would be recognized to be equivalents by a person skilled in the art.

The terms "soft-tack" and "tacky" as used herein refers to the ability of a surface to bind to other surfaces or objects in a more releasable and gentler manner than conventional adhesives. The degree of tackiness can be measured by the loop tack test (described below) and a soft tack coating or composition would typically measure greater than 0.3N. For example soft tack materials suitable for use in the present invention can range from 0.4 to about 2N, more suitable in some instances from about 0.5 to about 1.5N according to the loop tack test.

The soft-tack substrate, in certain embodiments, is preferably a soft material suitable for both capturing micrografts and providing a fluid seal with the skin graft transplantation site as described herein. For example, the substrate can comprise a silicone gel, a soft silicone, hydrocolloid, hydrogel, polyurethane gel, polyolefin gel, hydrogenated styrenic copolymer gels, a foamed gel, a soft closed cell foam such as polyurethanes and polyolefins, polyurethane, polyolefin, or hydrogenated styrenic copolymers coated with an adhesive described below. The substrate can have a thickness between about 500 microns (μm) and about 1000 microns (μm). In one embodiment, the substrate has a stiffness between about 5 Shore OO and about 80 Shore OO. The substrate can include hydrophobic or hydrophilic materials.

In some embodiments, the substrate may be a hydrophobic-coated material. For example, the substrate can be formed by coating a mesh or porous material, such as, for example, woven, nonwoven, molded, or extruded mesh with a hydrophobic material. The hydrophobic material for the coating may be a soft silicone, for example. Factors that may be utilized to control the ability of the substrate to capture skin grafts can include the diameter and number of the pores in the substrate, the thickness of the substrate, and the tackiness of the substrate.

Figure 1A:
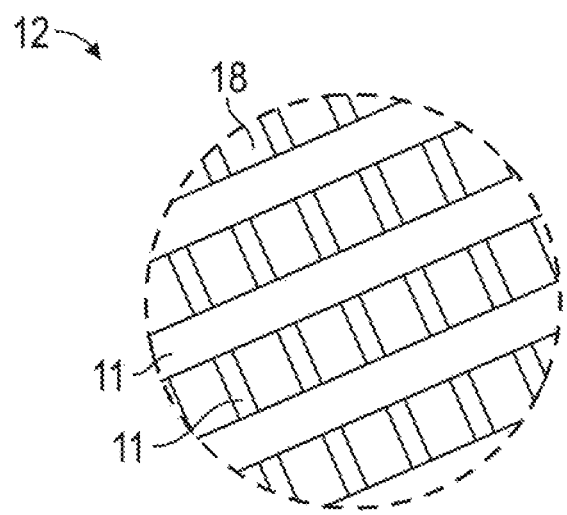
FIG. 1A is a more detailed schematic view of a portion of the soft-tack substrate of FIG. 1.

Referring to the drawings, FIGS. 1 and 1A depict an embodiment of a soft-tack substrate 10, viewed from the bottom, showing a soft-tack composition 12 having a lower surface 11 and a removable peripheral covering 13 for an optional peripheral adhesive element (e.g., for use when applying the substrate to a recipient site). The surface 11 provides a plurality of sites for capturing skin grafts. FIG. 1A is an expanded view of a portion of FIG. 1, showing an embodiment of the soft-tack composition. The soft-tack composition can also be porous and in this illustrated embodiment a plurality of pores 18 are disposed between the graft capture sites. In this embodiment, the substrate is formed of silicone-coated fibers 11 (described in more detail below). The pores 18 can be generally circular or elongated in one or more dimensions. Regardless of the shape or size of the pores 18, the porosity of the substrate 10 should be sufficient to permit fluid migration from a skin segment through the soft-tack surface 11.

Figure 2:
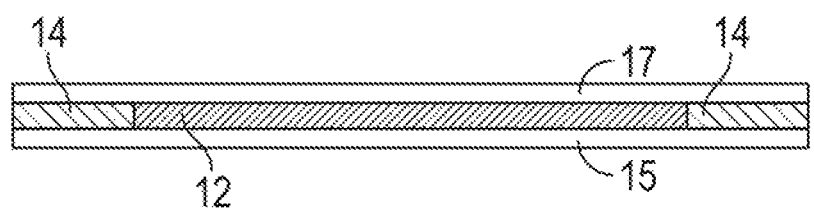
FIG. 2 is a schematic, side view of the substrate of FIG. 1 with protective upper and lower cover layers.

FIG. 2 is a side view of the substrate 10, showing the soft-tack composition 12, optional peripheral adhesive composition 14, and the first (bottom) and second (top) removable backings 15 and 17, respectively.

Figure 3:
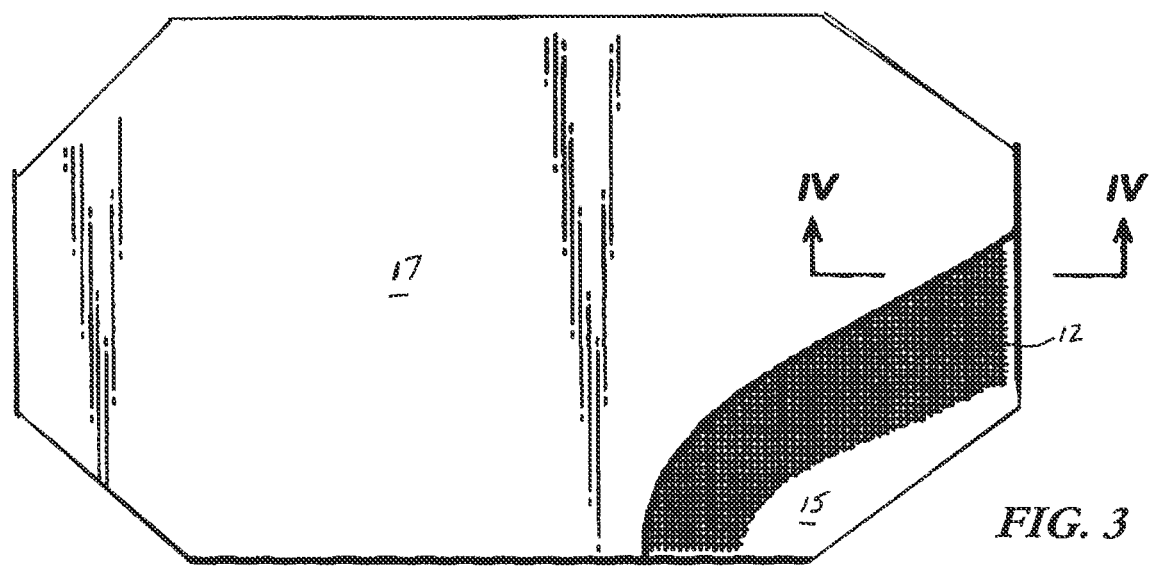
FIG. 3 is a perspective exploded view of the product of FIG. 2
Figure 4:
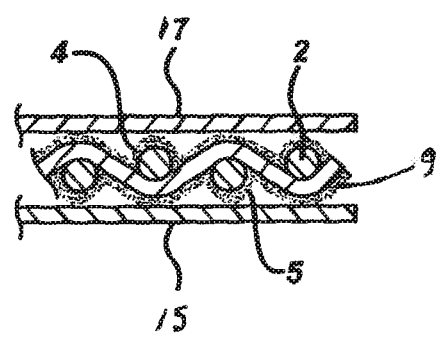
FIG. 4 is an enlarged partial cross-section view of the product of FIG. 3

Referring to FIGS. 3 and 4, a product according to the invention can comprise a substrate 12, e.g., of cellulose acetate gauze 2, having upper and lower surfaces 4,5 coated with a hydrophobic, tacky, crosslinked silicone gel 9. The silicone composition penetrates the gauze substrate to form a single, chemically homogeneous silicone phase on the upper and lower surfaces. The coated substrate 12 has an array of apertures extending through the substrate and the silicone to allow passage of wound fluid through the material. In some embodiments, the tackiness of the coated upper surface 4 can be approximately 50% greater than the tackiness of the coated lower surface 5, as determined by the loop tack test described below. The nominal weight of the gauze 2 can be, for example, 100 grams per square meter and the nominal total coating weight of the silicone can be 120-130 grams per square meter.

Identical release-coated cover sheets 15, 17 can be applied to the upper and lower silicone-coated surfaces 4, 5. In use, the lower release sheet 8 is removed first to expose the less tacky lower surface 5 of the substrate 12. It is relatively easy to selectively remove the lower release sheet 15 because of the lower adherence of this sheet to the material compared to the upper release sheet 17. The lower and/or upper release sheets may further comprise indicia to identify the release sheet to be removed first. The lower surface 5 may then be applied to a skin graft harvester bed, followed by removal of the upper release sheet 7 at the time of removal from the harvester or transplantation (or at the time of application of optional secondary dressing elements such as an absorbent layer, if desired).

Further details on manufacturing techniques for making soft-tack porous substrates can be found in U.S. Patent Application Pub. No. 2013/0165837 by Systagenix Would Management IP Co. BV entitled "Silicone Gel-Coated Wound Dressings," published Jun. 27, 2013, herein incorporated in its entirety by reference.

Figure 5:
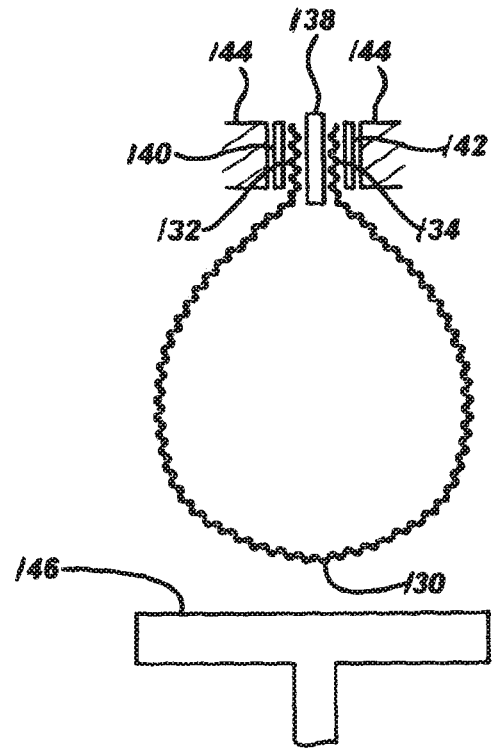
FIG. 5 shows a schematic diagram of the apparatus used for the loop tack measurement test.

The tackiness of the silicone coatings produced by the methods of the invention can be measured in a tensile tester, such as an Instron tester, using the set-up shown in FIG. 5. Samples of silicone coated gauze were cut to dimensions 5.times.9.5 cm. Margins of 1 cm were marked out along the long edges by drawing straight lines 1 cm from the long edges. The sheet of coated gauze 1130 was looped around and the 1 cm margins 132, 134 on opposed edges of one surface (opposite the surface being measured) were applied firmly to opposite sides of a 2 mm thick metal spacer bar 138. Strips of polypropylene film 1 cm wide 140, 142 were then applied to the opposite surfaces of the coated gauze opposite the spacer bar 138 to prevent the coated gauze from adhering to the jaws of the measurement device.

The assembly of polypropylene strips, coated gauze and spacer bar was then gripped in the jaws 144 of the Instron tester. The loop of coated gauze 130 having the surface under test outermost was then lowered onto a clean polycarbonate surface 146 of dimensions 15.5 cm.times.3.8 cm so that the loop adheres to the surface, and raised to detach the loop from the surface. Lowering and raising are performed at 300 mm/min, and the minimum distance between the jaws 44 and the polycarbonate surface 46 is 15 mm. The measured tack (in Newtons) is the maximum force measured while detaching the loop from the surface.

Figure 6A:
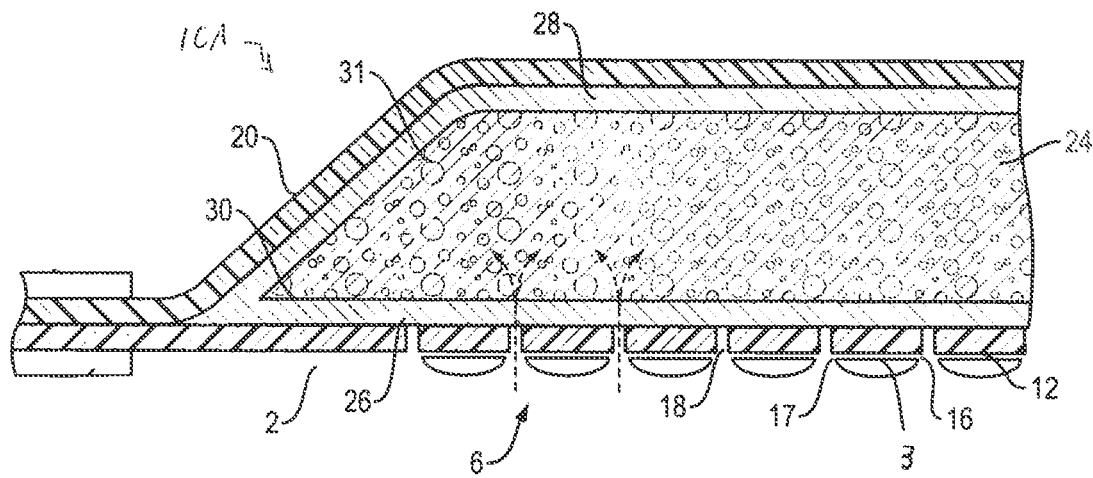
FIG. 6A is a partial cross-sectional view of an absorbent, soft-tack dressing according to the invention.

FIG. 6A is a partial cross-sectional view of an absorbent dressing incorporating a soft-tack, porous composition according to the invention. Soft-tack base layer 16 and sealing member 20 define an enclosure for an absorbent material 24. The figure also schematically shows a plurality of micrografts 4 carried on a bottom surface (e.g., a skin-contacting surface) of the base layer 12. A plurality of pores 18 in the base layer permit fluid ingress and provide passageways to the absorbent material 24. Optionally, one or more wicking layers can be utilized to distribute captured fluids to different portions of the absorbent material. In the illustrated embodiment, a first wicking layer 26 is disposed in proximity to the base layer and a second wicking layer 28 is disposed in proximity to the sealing member 28. Alternatively, wicking material can form alternating layers with absorbent material layers (sandwich style) or wicking material can be distributed throughout or otherwise dispersed within the absorbent material. In the illustrated embodiment, the first and second wicking layers 26, 28, respectively, can be joined together at the periphery to form a seal 30 that completely or substantially encloses the absorbent material.

Additionally, FIG. 6A shows the substrate 12 in use as part of dressing 10A applied to a skin graft transplantation site on a surface of a patient's skin 2 in need of grafting. On the bottom surface of the base layer 12 are a plurality of captured skin grafts 3, which are placed in contact with the skin 2 as the substrate 10 is applied. Fluid migration from the transplant site and extraction into the absorbent material 24 is illustrated by the dotted lines.

Figure 6B:
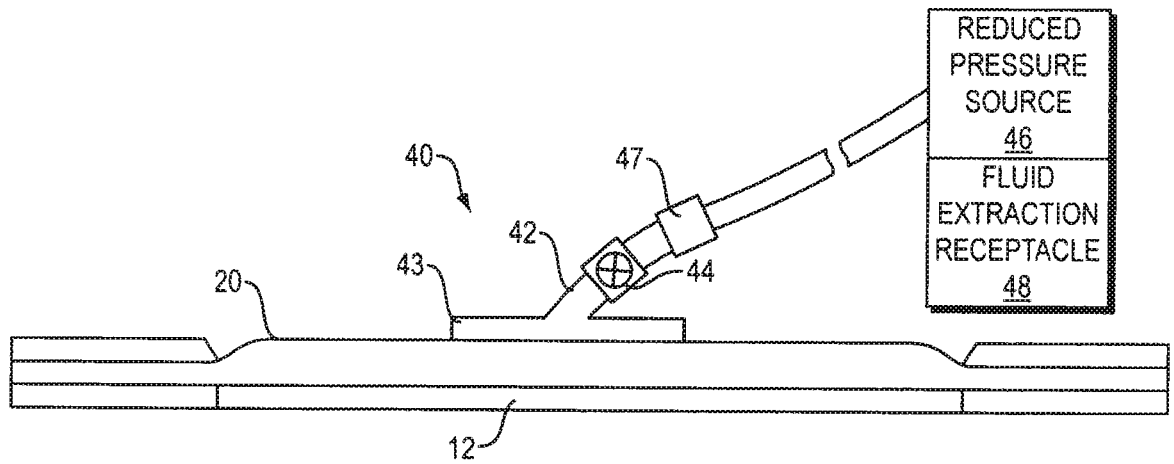
FIG. 6B is a schematic, side view of an alternative embodiment of an absorbent substrate according to the invention having a port for coupling to a reduced pressure source or external fluid drainage receptacle.

FIG. 6B shows another embodiment of an absorbent substrate, having the soft-tack porous substrate 12, sealing member 20 and a port 40 for coupling to a source of negative pressure 46 and/or a fluid extraction receptacle 48. The port 40 can further include a conduit 42, one or more filters 47 and/or a check valve 44 to permit fluid extraction (and, optionally, one-way flow) from the absorbent material, e.g., in instances where the absorbent material reaches or nears a saturated state to an external fluid receptacle or a waste disposal site.

Continuing with FIGS. 6A-B, the sealing member 20 has a periphery and a central portion. The periphery of the sealing member 20 may be positioned proximate the periphery of the base layer 12 such that the central portion of the sealing member 20 and the central portion of the base layer 12 define an enclosure.

The sealing member 20 may cover the tissue site 6 to provide a fluid seal and a sealed space between the tissue site 6 and the sealing member 20 of the substrate 10. Further, the sealing member 20 may cover tissue, such as a portion of the epidermis 106, surrounding the tissue site 6 to provide the fluid seal.

The sealing member 20 may be formed from any material that allows for a fluid seal. A fluid seal is a seal adequate to maintain reduced pressure at a desired site given the particular reduced pressure source or system involved. The sealing member 20 may comprise, for example, one or more of the following materials: hydrophilic polyurethane; cellulosics; hydrophilic polyamides; polyvinyl alcohol; polyvinyl pyrrolidone; hydrophilic acrylics; hydrophilic silicone elastomers; an INSPIRE 2301 material from Expopack Advanced Coatings of Wrexham, United Kingdom having, for example, an moisture vapor transmission rate (MVTR) (inverted cup technique) of 14400 g/m$^2$/24 hours and a thickness of about 30 microns; a thin, uncoated polymer drape; natural rubbers; polyisoprene; styrene butadiene rubber; chloroprene rubber; polybutadiene; nitrile rubber; butyl rubber; ethylene propylene rubber; ethylene propylene diene monomer; chlorosulfonated polyethylene; polysulfide rubber; polyurethane (PU); EVA film; co-polyester; silicones; a silicone drape; a 3M Tegaderm® drape; a polyurethane (PU) drape such as one available from Avery Dennison Corporation of Pasadena, Calif.; polyether block polyamide copolymer (PEBAX), for example, from Arkema, France; or other appropriate material.

The sealing member 20 may allow vapor to exit while inhibiting liquids from exiting the sealed space provided by the substrate 10. The sealing member 20 may be a flexible, breathable film having a high MVTR of, for example, at least about 300 g/m$^2$ per 24 hours. The sealing member 20 may comprise a range of medically suitable films having a thickness between about 15 microns (μm) to about 50 microns (μm). In other embodiments, a low or no vapor transfer drape can be used as the sealing member.

The fluid management assembly may be disposed in the enclosure 31 and may include a first wicking layer 26, a second wicking layer 28, and an absorbent layer 24. The absorbent layer 24 may be positioned in fluid communication between the first wicking layer 26 and the second wicking layer 28. The first wicking layer 26 may have a grain structure (not shown) adapted to wick fluid along a surface of the first wicking layer 26. Similarly, the second wicking layer 28 may have a grain structure (not shown) adapted to wick fluid along a surface of the second wicking layer 28. For example, the first and the second wicking layer 26, 28 may wick or otherwise transport fluid in a lateral direction along the surfaces of the first and the second wicking layer 26, 28, respectively. The surfaces of the first and the second wicking layer 26, 28 may be normal relative to the thickness of each of the first and the second wicking layer 26, 28. The wicking of fluid along the first and the second wicking layers 26, 28 may enhance the distribution of the fluid over a surface area of the absorbent layer 24 that may increase absorbent efficiency and resist fluid blockages. Fluid blockages may be caused, for example, by fluid pooling in particular location in the absorbent layer 24 rather than being distributed more uniformly across the absorbent layer 24. The laminate combination of the first and the second wicking layer 26, 28 and the absorbent layer 24 may be adapted as described above to maintain an open structure, resistant to blockage, that can maintain fluid communication with, for example, the tissue site 6.

The dressing 10A may include, without limitation, any number of wicking layers and absorbent layers as desired for treating a particular tissue site. For example, the absorbent layer 24 may be a plurality of absorbent layers 24 positioned in fluid communication between the first wicking layer 26 and the second wicking layer 28 as described above. Further, at least one intermediate wicking layer may be disposed in fluid communication between the plurality of absorbent layers 24. Similar to the absorbent layer 24 described above, the plurality of absorbent layers 24 and the at least one intermediate wicking layer may be positioned within the wicking layer enclosure.

In one embodiment, the absorbent material or layer 24 may be a hydrophilic material adapted to absorb fluid from, for example, the tissue site 6. Materials suitable for the absorbent layer 184 may include Luquafleece® material, Texus FP2326, BASF 402c, Technical Absorbents 2317 available from Technical Absorbents (www.techabsorbents.com), sodium polyacrylate super absorbers, cellulosics (carboxy methyl cellulose and salts such as sodium CMC), or alginates. Materials suitable for the first and second wicking layers 26, 28 may include any material having a grain structure capable of wicking fluid as described herein, such as, for example, Libeltex TDL2 80 gsm.

The substrate 10A can be a pre-laminated structure manufactured at a single location or simply individual layers of material stacked upon one another as described above. Individual layers of the substrate 10 may be bonded or otherwise secured to one another without adversely affecting fluid management by, for example, utilizing a solvent or non-solvent adhesive, or by thermal welding.

In one embodiment, the enclosure 31 defined by the base layer 12 and the sealing member 20 may include an anti-microbial layer. The addition of the anti-microbial agent may reduce the probability of excessive bacterial growth within the dressing 10 to permit the dressing 10 to remain in place for an extended period. The anti-microbial material may be, for example, an additional layer included as a part of the substrate 10 as depicted in FIGS. 1-4, or a coating of an anti-microbial agent disposed in any suitable location within the substrate 10. The anti-microbial material may include elemental silver or similar compounds, for example.

Referring now to FIG. 6B, the port 40 for coupling to a source of reduced pressure can be positioned proximate to the sealing member 20 and in fluid communication with the absorbent material 24 through an aperture (not shown) in the sealing member 20 to provide reduced pressure from the reduced-pressure source 46 to the substrate 10. The port 40 may comprise a medical-grade, soft polymer or other pliable material. As non-limiting examples, the port 40 may be formed from polyurethane, polyethylene, polyvinyl chloride (PVC), fluorosilicone, or ethylene-propylene, etc. In one illustrative, non-limiting embodiment, port 40 may be molded from DEHP-free PVC. The port 40 may be formed in any suitable manner such as by molding, casting, machining, or extruding. Further, the port 40 may be formed as an integral unit or as individual components and may be coupled to the substrate 10 by, for example, adhesive, welding or mechanical coupling.

The port 40 can also include one or more filters 47, e.g., an odor filter to inhibit the passage of odors from the tissue site 6 out of the sealed substrate 10, or a hydrophobic filter.

The filter 47 can be disposed in the conduit 42 or other suitable location such that fluid communication between the reduced-pressure source 46 and the substrate is provided through the filter 47. In another embodiment, the filters 47 can be positioned in any exit location in the substrate 10, such as an aperture (not shown), that is in fluid communication with the atmosphere or with the reduced-pressure source 46. The filter 47 may also be positioned in any suitable location in the substrate that is in fluid communication with the graft transplantation site 6.

For example, an odor filter 47 may include a carbon material in the form of a layer or particulate, such as a woven carbon cloth filter such as those manufactured by Chemviron Carbon, Ltd. of Lancashire, United Kingdom (www.chemvironcarbon.com). A hydrophobic filter 47 may be comprised of a material that is liquid impermeable and vapor permeable, such as a material manufactured under the designation MMT-314 by W.L. Gore & Associates, Inc. of Newark, Del., United States, or similar materials.

Continuing with FIG. 6B, the reduced-pressure source 46 provides reduced pressure to the substrate 10 and the sealed space 31. The reduced-pressure source 46 may be any suitable device for providing reduced pressure as described herein, such as, for example, a vacuum pump, wall suction, or other source. Additional details on reduced pressure sources can be found, for example, in U.S. patent application Ser. No. 11/646,918 filed Dec. 28, 2006; U.S. patent application Ser. No. 11/810,027 filed Jun. 4, 2007; U.S. patent application Ser. No. 12/661,293 filed Mar. 15, 2010; and U.S. patent application Ser. No. 13/052,873 filed Mar. 21, 2011. The disclosures of each of these patent applications are incorporated by reference in their entireties.

As used herein, "reduced pressure" generally refers to a pressure less than the ambient pressure at a tissue site being subjected to treatment. Typically, this reduced pressure will be less than the atmospheric pressure. The reduced pressure may also be less than a hydrostatic pressure at a tissue site. Unless otherwise indicated, values of pressure stated herein are gauge pressures. While the amount and nature of reduced pressure applied to a tissue site will typically vary according to the application, the reduced pressure will typically be between −5 mmHg and −500 mmHg, and more typically in a therapeutic range between −100 mmHg and −200 mmHg.

The reduced pressure delivered may be constant or varied (e.g., patterned or random) and may be delivered continuously or intermittently. Although the terms "vacuum" and "negative pressure" may be used to describe the pressure applied to the tissue site, the actual pressure applied to the tissue site may be more than the pressure normally associated with a complete vacuum. Consistent with the use herein, an increase in reduced pressure or vacuum pressure typically refers to a relative reduction in absolute pressure. An increase in reduced pressure corresponds to a reduction in pressure (more negative relative to ambient pressure) and a decrease in reduced pressure corresponds to an increase in pressure (less negative relative to ambient pressure).

A conduit 42 having an internal lumen may be coupled in fluid communication between the reduced-pressure source 46 and the substrate 10. The conduit interface 43 may be coupled in fluid communication with the dressing and adapted to connect between the conduit 42 and the substrate 10 for providing fluid communication with the reduced-pressure source 46. The conduit interface 43 may be fluidly coupled to the conduit 42 in any suitable manner, such as, for example, by an adhesive, solvent or non-solvent bonding, welding, or interference fit. An aperture (not shown) in the sealing member 20 may provide fluid communication between the substrate and the conduit interface 43. In one embodiment, the conduit 42 may be inserted into the substrate 10 through an aperture (not shown) in the sealing member 20 to provide fluid communication with the reduced-pressure source 46 without utilization of the conduit interface 43. The reduced-pressure source 46 may also be directly coupled in fluid communication with the substrate 10 and/or the sealing member 20. The conduit 42 may be, for example, a flexible polymer tube. A distal end of the conduit 42 may include any one of known couplings for attachment to the reduced-pressure source 46.

Figure 7:
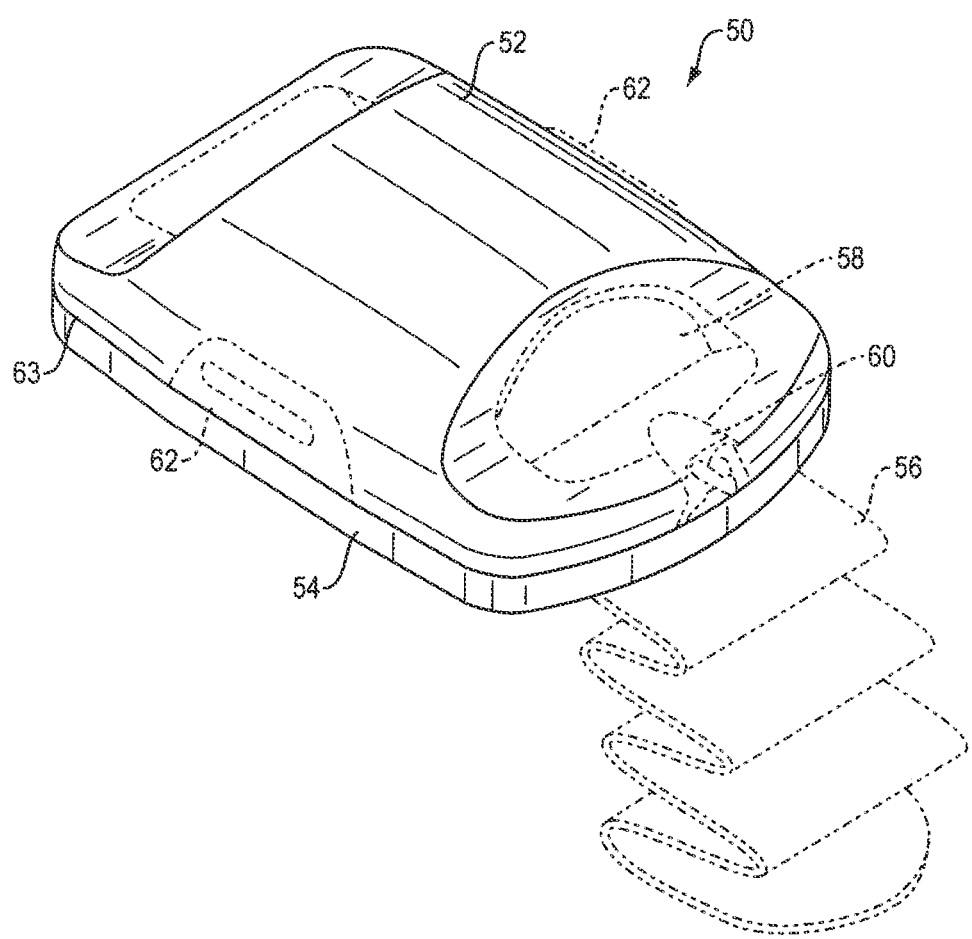
FIG. 7 is a schematic, perspective top view of a skin graft harvester for use with the soft-tack substrate.

FIG. 7 is a schematic view of a skin graft harvester 50 for use with a soft-tack substrate in accordance with various aspects of the present invention. In this illustrative embodiment, the harvest 50 includes a detachable head portion 52 and harvester body 54. The harvester body 54 is adapted for placement on a patient's skin at a donor site where skin grafts are to be obtained, e.g., on the inner thigh, and secured in place, for example, with strap 56 (shown in phantom). The head 52 can further include a heater (not shown) powered via a coupler 60 adapted to couple with a power source in a base unit (not shown). The head 52 further includes a seal 63 which permits a reduced pressure chamber to be formed when the head 52 and body 54 are joined together and the harvester 50 is coupled to a vacuum pump or other source of reduced pressure, e.g., via coupler 60 connecting the harvester 50 to its base unit. The head 52 can further include one or more windows 58 for observation of skin blisters being formed within the chamber by application of reduced pressure, heat or both. Once the blisters have been formed, the head 52 can be removed, e.g., by deactivating the source of reduced pressure and by actuation of release levers 62, which break the seal 63 and allow the head 52 to be lifted off the harvester body 54.

Additional details on harvesters useful in connection with the present invention can be found in U.S. patent application Ser. No. 13/839,518 filed Mar. 15, 2013; U.S. patent application Ser. No. 13/346,329 filed Jan. 9, 2012; U.S. patent application Ser. No. 13/436,318 also filed Jan. 9, 2012; U.S. patent application Ser. No. 13/014,737 filed Jan. 27, 2011; U.S. patent application Ser. No. 12/851,656 filed Aug. 6, 2010; U.S. patent application Ser. No. 12/851,621 filed Aug. 6, 2010; U.S. patent application Ser. No. 12/851,703 filed Aug. 6, 2010; and U.S. patent application Ser. No. 12/851,682 filed Aug. 6, 2010. The contents of each of the above-referenced related applications are herein incorporated by reference in their entireties.

Figure 8:
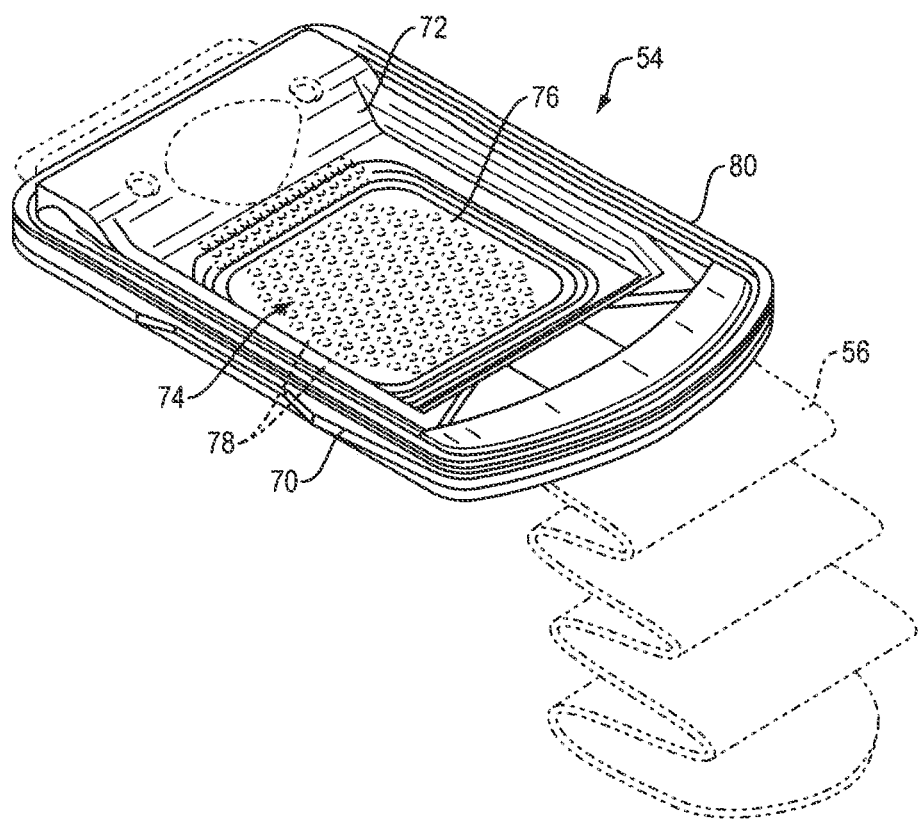
FIG. 8 is a schematic, perspective top view of the skin graft harvester of FIG. 7 with the head component removed and the cutter mechanism exposed.

FIG. 8 is a schematic view of the skin graft harvester 50 of FIG. 7 with the head 52 removed and the cutting mechanism 74 exposed. The harvester body 54 can include a base portion 70, a sled 72, and actuator handle 80. The cutting mechanism 74 can include a plurality of plates with initially aligned holes through which skin blisters are drawn by heat and/or application of suction when the head 52 is joined to the harvester body 54 and activated. Once the blisters are formed, they can be cleaved by the cutting mechanism 74. For example, below the top plate depicted in FIG. 8, one or more additional plates, e.g., a cutter plate and a bottom plate can be deployed with aligned holes. By actuation (e.g., pulling up) of handle 80, the sled 72 is caused to move horizontally such that one of the plates below the top plate, e.g., the "cutter plate" (not shown) also moves (because of its linkage to the sled 72), thereby occluding the alignment of holes 78 and cleaving the raised blisters from the donor's skin.

Figure 9:
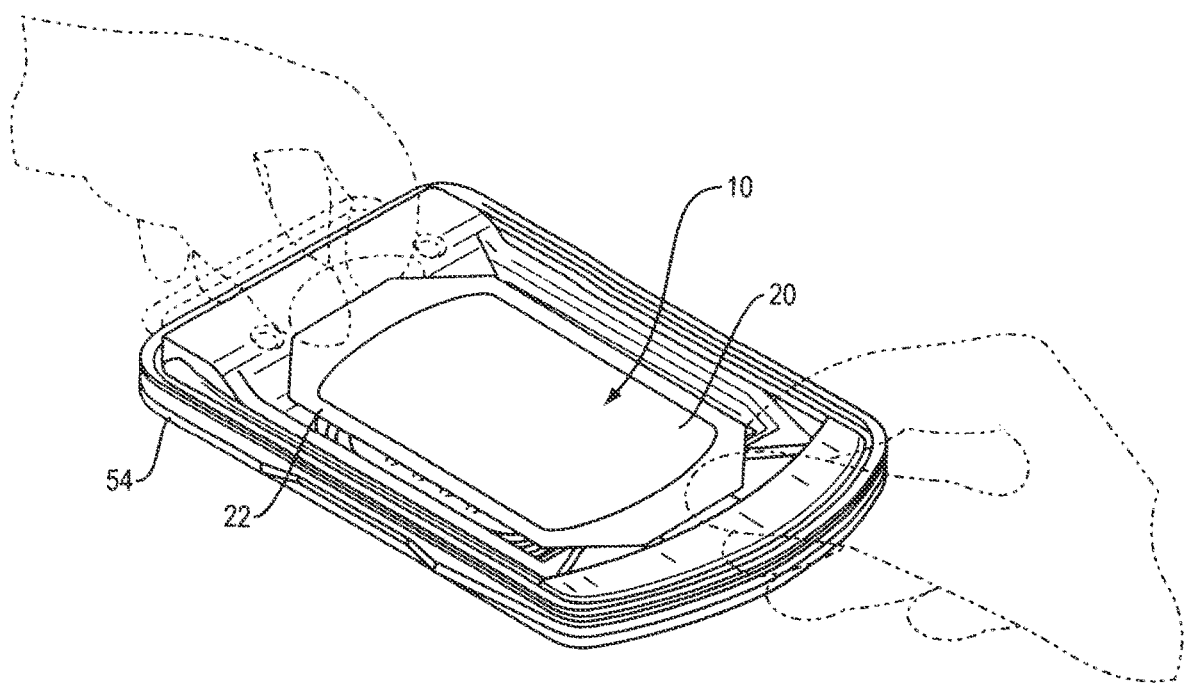
FIG. 9 is a schematic, perspective top view of the skin graft harvester of FIG. 7 with a soft-tack substrate according to the invention deployed in the harvester to capture skin grafts.

FIG. 9 is a schematic view of the skin graft harvester 50 of FIG. 7 with a soft-tack substrate 10 according to the invention deployed in the harvester body 54 to capture skin grafts. In the illustrated embodiment, the user (e.g., clinician) places the substrate 10 in the harvester holding the backing 22 with the upper cover sheet (or upper sealing member 20) upwards and the lower soft-tack surface (not visible) in contact with the top plate of cutter mechanism (as shown in FIG. 8). By so placing the substrate, the lower soft-tack surface will also come into contact with the skin blisters. In one preferred embodiment, the substrate is so situated before the cutter mechanism is actuated to cleave the blisters into skin grafts (as described above). In other embodiments, the substrate can be placed onto the harvester after cleavage to capture grafts that have already been cleaved from the skin. In either event the substrate can then be removed from the harvester body 54 and applied to a recipient site, as illustrated in FIGS. 1-6.

Although this specification discloses advantages in the context of certain illustrative, non-limiting embodiments, various changes, substitutions, permutations, and alterations may be made without departing from the scope of the specification as defined by the appended claims. Further, any feature described in connection with any one embodiment may also be applicable to any other embodiment

What is claimed is:

1. An apparatus comprising:
a substrate formed from a fibrous material comprising an upper surface, and a lower surface configured for placement on an excised skin graft at a donor site, the upper and lower surfaces coated with a silicone composition to form a homogeneous silicone phase, and the lower surface comprising a plurality of skin graft capture sites disposed thereon, the plurality of skin graft capture sites being configured to contact the excised skin graft and capture the excised skin graft for removal from the donor site, wherein the silicone phase on the upper surface and lower surface are configured such that the upper surface comprises a tackiness of approximately 50% greater than tackiness of the lower surface;
a plurality of pores extending through the substrate and the silicone phase and configured to allow passage of fluids therethrough;
a peripheral adhesive composition disposed outwardly from a lateral border of the substrate and having an upper surface and a lower surface;
a first removeable backing sheet covering the lower surface of the substrate and the lower surface of the peripheral adhesive composition, and a second removable backing sheet covering the upper surface of the substrate and the upper surface of the peripheral adhesive composition;
a skin graft harvestor having a body portion and a detachable head portion, the body portion having an opening for placement around the skin graft capture sites,
wherein the substrate is positionable over the opening, and a border region of the lower surface is releasably adherable to the body portion about the opening for capturing the excised skin graft;
wherein the excised skin graft is adherable to the substrate by the lesser tackiness of the lower surface.

2. The apparatus of claim 1, wherein the silicone phase comprises an average thickness between about 500 microns (µm) and about 1000 microns (µm).

3. The apparatus of claim 1, wherein the fibrous material comprises a plurality of microfibers having an average diameter of about 0.1 to about 10 micrometers.

4. The apparatus of claim 1, wherein the fibrous material comprises a plurality of nanofibers having an average diameter of about 1 to about 100 nanometers.

5. The apparatus of claim 1, wherein the fibrous material comprises a plurality of nanofibers having an average diameter of about 20 to about 80 nanometers.

6. The apparatus of claim 1, wherein the plurality of pores comprise an average cross-section dimension ranging from about 1 nanometer to about 1 millimeter.

7. The apparatus of claim 6, wherein the plurality of pores comprise an average cross-section dimension ranging from about 1 nanometer to about 100 micrometers.

8. The substrate of claim 1, further comprising at least one port for coupling to a reduced pressure source and wherein the at least one port comprises a valve.

9. The substrate of claim 8, wherein the port further comprises a conduit configured to provide fluid communication between the absorbent material or at least one wicking layer within the chamber to an external fluid receptacle.

10. The apparatus of claim 1, wherein the substrate further comprises at least a first removable backing associated with a base layer for handling the substrate prior to positioning in the skin graft harvester and a second removable backing for handling the substrate and the skin graft prior to positioning at a recipient site.

11. The apparatus of claim 1, wherein the dressing further comprises an absorbent material.

12. The apparatus of claim 11, wherein the absorbent material comprises an open cell foamed polymer.

13. The apparatus of claim 11, wherein the absorbent material comprises a plurality of pores each having an average cross-section dimension ranging from about 0.05 millimeters to about 5 millimeters.

14. The apparatus of claim 11, wherein the absorbent material comprises a plurality of pores each having an average cross-section dimension ranging from about 0.1 millimeters to about 1 millimeters.

15. The apparatus of claim 11, wherein the absorbent material is selected from group comprising silicones, silicone gels, soft silicones, hydrocolloids, hydrogels, polyurethanes, polyurethane gels, polyolefins, polyolefin gels, hydrogenated styrenic copolymers, hydrogenated styrenic copolymer gels, foamed gels and combinations thereof.

16. The apparatus of claim 1, wherein the silicone phase comprises a degree of tackiness in a range of about 0.4N to about 2N.

\* \* \* \* \*